United States Patent [19]

Yoshimura et al.

[11] Patent Number: 5,411,934
[45] Date of Patent: May 2, 1995

[54] ALKANOIC ACID AMIDE DERIVATIVE OR ITS SALT, PROCESS FOR PRODUCING THE SAME AND HERBICIDAL COMPOSITION

[75] Inventors: Takumi Yoshimura; Keiji Toriyabe; Katsumi Masuda; Ryo Hanai, all of Shizuoka, Japan

[73] Assignees: Kumiai Chemical Industry Co., Ltd.; Ihara Chemical Industry Co., Ltd., both of Tokyo, Japan

[21] Appl. No.: 916,127
[22] PCT Filed: Nov. 29, 1991
[86] PCT No.: PCT/JP91/01649
  § 371 Date: Jul. 30, 1992
  § 102(e) Date: Jul. 30, 1992
[87] PCT Pub. No.: WO92/09584
  PCT Pub. Date: Jun. 19, 1992

[30] Foreign Application Priority Data

Nov. 30, 1990 [JP] Japan .................. 2-330168

[51] Int. Cl.⁶ ............... C07D 239/52; C07D 239/42; C07D 239/26; A01N 43/54
[52] U.S. Cl. ................. 504/239; 504/242; 504/243; 504/193; 544/229; 544/319; 544/327; 544/328; 544/329; 544/333; 544/335; 544/334
[58] Field of Search ......... 544/335, 334, 329, 327, 544/326, 319, 333, 328, 229; 504/239, 242, 243

[56] References Cited

U.S. PATENT DOCUMENTS

| | | | |
|---|---|---|---|
| 5,053,072 | 10/1991 | Ort et al. | 544/228 |
| 5,238,907 | 8/1993 | Kruger et al. | 504/243 |
| 5,317,005 | 5/1994 | Jones | 504/239 |

FOREIGN PATENT DOCUMENTS 0353640 7/1989 European Pat. Off. .
2-282371 11/1990 Japan .
WO92/01677 2/1992 WIPO .

OTHER PUBLICATIONS

Yamanaka et al., Chemical Abstracts, vol. 96, entry 68932t (1982).
Chemical Abstract, vol. 117, 1992, AN-2825f, JP-A-04 54 168, Feb. 21, 1992.

*Primary Examiner*—John M. Ford
*Attorney, Agent, or Firm*—Oblon, Spivak, McClelland, Maier & Neustadt

[57] ABSTRACT

The present invention provides a novel alkanoic acid amide derivative of the formula,

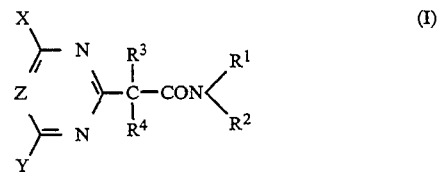

(wherein $R^1$ is a hydrogen atom, an alkyl group or an alkoxyalkoxy group, $R^2$ is a group of -$SO_2R$ or a hydroxyl group, $R^5$ is an alkyl group, $R^3$ is an alkyl group, a cycloalkyl group, a cycloalkenyl group or a phenyl group, $R^4$ is a hydrogen atom or an alkyl group, X and Y may be the same or different and are an alkoxy group, an alkylamino group or a dialkylamino group, and Z is a methine group or a nitrogen atom) and its salt, a process for preparing the same and a herbicidal composition containing the same as an effective ingredient.

This compound kills annual and perennial weeds grown in paddy fields and upland fields at a small dose, and is safe to a useful crop plant.

12 Claims, No Drawings

ALKANOIC ACID AMIDE DERIVATIVE OR ITS SALT, PROCESS FOR PRODUCING THE SAME AND HERBICIDAL COMPOSITION

This application claims priority under 35 U.S.C. §365(a) to International Patent Application PCT/JP91/01649 filed Nov. 29, 1991, and from thence under 35 U.S.C. §119 to Japanese patent application no. 330168/1990 filed Nov. 30, 1990.

TECHNICAL FIELD

The present invention relates to novel alkanoic acid amide derivatives and their salts, and herbicidal compositions containing them, which are useful for application to paddy fields, upland fields and non-agricultural fields.

BACKGROUND ART

In recent years, many herbicides have been developed, and have contributed to the improvement of productivity and to energy saving for agricultural works. However, since many of these herbicides work specifically on respective crop plants and weeds, it is necessary to selectively use depending on the individual types of cropplants and places to be applied, so as to be most effective. Therefore, it is always an important subject matter in this field to develop a novel compound having a herbicidal effect.

An object of the present invention is to provide a novel herbicidal composition containing a compound having a chemical structure different from those of conventional herbicides as an effective ingredient, which can be many-sidedly used for the cultivation of various crop plants.

As a result of the study for achieving the abovementioned object, the present inventors have discovered that a sort of an alkanoic acid amide derivative having a pyrimidine ring or a triazine ring or its salt is effective for killing various weeds, and is safe to crop plants. The present invention has been achieved on the basis of this discovery.

DISCLOSURE OF THE INVENTION

The present invention relates to an alkanoic acid amide derivative of the following formula (I) and its salt:

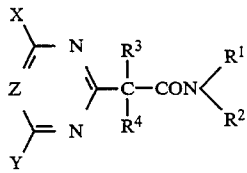

wherein $R^1$ is a hydrogen atom, a hydroxy group, a $C_1$-$C_8$ alkyl group (which may be substituted with a $C_1$-$C_8$ alkoxy group, a benzyloxy group, a $C_1$-$C_8$ alkoxy $C_1$-$C_8$ alkoxy group, a $C_1$-$C_8$ alkoxycarbonyl group, a $C_1$-$C_3$ alkylthio group or a phenyl group), a $C_2$-$C_6$ alkenyl group, a $C_2$-$C_6$ alkynyl group, a $C_1$-$C_8$ alkoxy group, a benzyloxy group, a $C_2$-$C_6$ alkenyloxy group, or a $C_2$-$C_6$ alkynyloxy group; $R^2$ is a hydroxy group, a $C_1$-$C_8$ alkoxy group, a benzyloxy group, a $C_2$-$C_6$ alkenyloxy group, a cyano group, a phenyl group (which may be substituted with a $C_1$-$C_8$ alkyl group, a trifluoromethyl group, a halogen atom or a nitro group), an amino group, a $C_1$-$C_8$ alkylsulfonylamino group or a group of -$SO_2R^5$ ($R^5$ is a $C_1$-$C_8$ alkyl group (which may be substituted with a $C_1$-$C_8$ alkoxy group or a halogen atom), a $C_2$-$C_6$ alkenyl group, a $C_3$-$C_8$ cycloalkyl group, a $C_1$-$C_8$ alkylamino group, a di-$C_1$-$C_8$ alkylamino group, a 1-pyrrolidinyl group or an anilino group); $R^3$ is a hydrogen atom, a $C_1$-$C_8$ alkyl group (which may be substituted with a hydroxy group, a $C_1$-$C_8$ alkoxy group, a phenoxy group, a $C_1$-$C_8$ alkylthio group, a phenylthio group, a trimethylsilyl group, a $C_3$-$C_8$ cycloalkyl group, a phenyl group or a di-$C_1$-$C_8$ alkylamino group), a $C_2$-$C_6$ alkenyl group (which may be substituted with a halogen atom), a $C_2$-$C_6$ alkynyl group, a $C_3$-$C_8$ cycloalkyl group (which may be substituted with a $C_1$-$C_3$ alkyl group), a $C_3$-$C_6$ cycloalkenyl group, a phenyl group (which may be substituted with a $C_1$-$C_8$ alkyl group or a halogen atom), a tetrahydrothienyl group or a tetrahydrofuryl group; $R^4$ is a hydrogen atom or a $C_1$-$C_8$ alkyl group; X and Y may be the same or different, and are a hydroxy group, a halogen atom, a $C_1$-$C_8$ alkyl group, a $C_1$-$C_8$ haloalkyl group, a $C_1$$C_8$ alkoxy $C_1$-$C_8$ alkyl group, a $C_1$-$C_8$ alkoxy group, a phenoxy group (which may be substituted with a $C_1$-$C_8$ alkyl group), a $C_1$-$C_8$ haloalkoxy group, a $C_2$-$C_6$ alkenyloxy group, a $C_2$-$C_6$ alkynyloxy group, a $C_1$-$C_8$ alkylthio group, a phenylthio group, an amino group, a $C_1$-$C_8$ alkylamino group, a di-$C_1$-$C_8$ alkylamino group or a pyrrolidino group; and Z is a methine group or a nitrogen atom.

Among the compounds of the present invention, a part includes their optical isomers and geometrical isomers.

The compound (I) and its salt of the present invention can be prepared, for example, by the following Preparation Processes (1)-(3). However, the preparation processes should not be limited thereto.

Preparation Process (1)

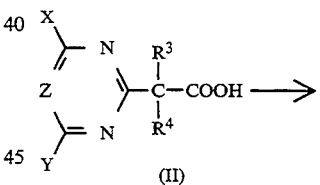

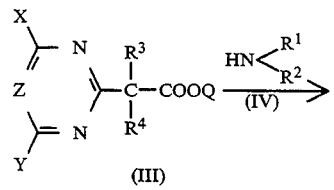

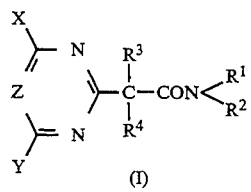

(wherein Q is a halogen atom, a cyano group, an imidazolyl group or a substituted amidinoxy group, and $R^1$, $R^2$, $R^3$, $R^4$, X, Y and Z are as defined above)

The compound of the formula (I) can be prepared by reacting a compound of the formula (II) with an equivalent or more amount of a condensation agent in an appropriate solvent at a temperature in the range of from −10° C. to a boiling point of the solvent for from 0.5 to 24 hours to obtain a compound of the formula (III), reacting the resultant isolated or not isolated compound with a compound of the formula (IV), together with the equivalent or more amount of a base in an appropriate solvent at a temperature in the range of from −10° C. to a boiling point of the solvent for from 0.5 to 24 hours, and then acidifying.

In this preparation process, as the condensation agent, there can be used thionyl chloride, oxalic acid dichloride, chlorocarbonic acid ester, carbonyl diimidazole, cyanophosphoric acid ester, carbodiimides or the like. As the base, there can be used alkali metals such as metallic sodium and metallic potassium; alkali metal hydrides and alkali earth metal hydrides such as sodium hydride, potassium hydride and calcium hydride; organic alkali metals such as n-butyl lithium and lithium diisopropylamide; alkali metal alkoxides such as potassium t-butoxide; alkali metal carbonates such as sodium carbonate and potassium carbonate; alkali metal hydrogen carbonates such as sodium hydrogen carbonate and potassium hydrogen carbonate; alkali metal hydroxides such as sodium hydroxide and potassium hydroxide; and organic amines such as triethylamine and pyridine. As the solvent, there can be used hydrocarbon type solvents such as benzene, toluene and xylene; halogenated hydrocarbon type solvents such as methylene chloride and chloroform; ether type solvents such as diethyl ether, tetrahydrofuran and 1,4-dioxane; ketone type solvents such as acetone and methyl ethyl ketone; ester type solvents such as methyl acetate and ethyl acetate; aprotic polar solvents such as dimethylformamide, dimethylacetamide and dimethylsulfoxide; and other acetonitrile.

Preparation Process (2)

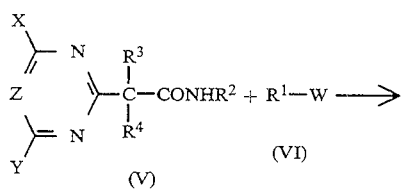

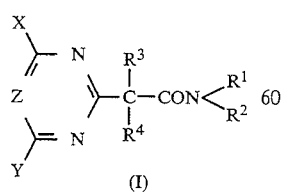

(wherein W is a halogen atom, an alkylsulfonyloxy group, a phenylsulfonyloxy group, a substituted phenylsulfonyloxy group or a trifluoromethylsulfonyloxy group, and X, Y, Z, $R^1$, $R^2$, $R^3$ and $R^4$ are as defined above).

The compound of the formula (I) can be prepared by reacting a compound of the formula (V) with a compound of the formula (VI) in the presence of an equivalent or more amount of a base in an appropriate solvent at a temperature in the range of from −70° C. to a boiling point of the solvent for from 0.5 to 24 hours.

The same base and solvent as illustrated in the above Preparation Process (1) can be used also in this preparation process.

Preparation Process (3)

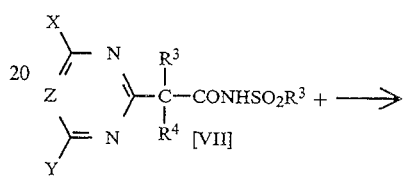

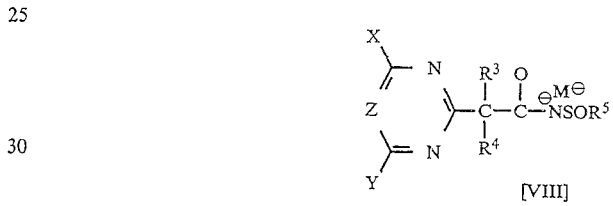

(wherein M is an alkali metal, an alkali earth metal, a transition metal, an ammonium or organic ammonium ion, and $R^3$, $R^4$, $R^5$, X, Y and Z are as defined above).

The compound of the formula (VIII) can be prepared by reacting a compound of the formula (VII) with an equivalent or more amount of a base in an appropriate solvent at a temperature in the range of from 0° C. to a boiling point of the solvent for from 5 to 24 hours, or with a transition metal salt such as cupric chloride in an appropriate solvent and a temperature in the range of from 0° C. to a boiling point of the solvent for from 0.5 to 24 hours.

In this preparation process, as the base, there can be used alkali metals such as metallic sodium and metallic potassium; alkali metal hydrides and alkali earth metal hydrides such as sodium hydride, potassium hydride and calcium hydride; alkali metal alkoxides such as potassium t-butoxide; alkali metal carbonates and alkali earth metal carbonates such as sodium carbonate, potassium carbonate and calcium carbonate; alkali metal hydroxides and alkali earth metal hydroxides such as sodium hydroxide, potassium hydroxide and calcium hydroxide; ammonia; and other organic amines such as isopropylamine. The same solvent as illustrated in the above Preparation Process (1) can be used also in this preparation process.

The compound of the formula (II) can be prepared, for example, in accordance with the following reaction route.

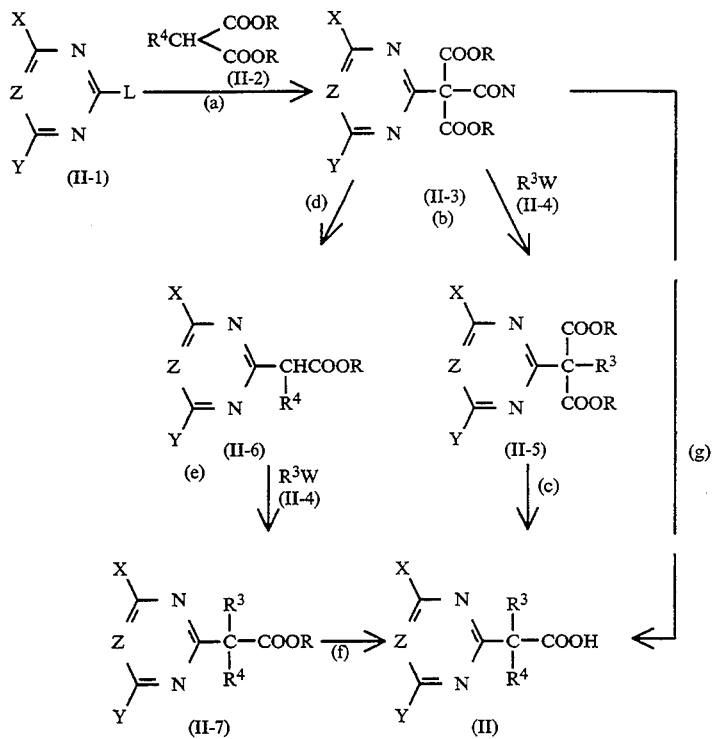

(wherein L is a halogen atom, an alkylsulfonyl group, benzylsulfonyl group or a substituted benzylsulfonyl group; R is an alkyl group; and X, Y, Z, $R^3$, $R^4$ and W are as defined above).

The steps for preparing the compound of the formula (II) are explained hereinafter.

Step (a)

The compound of the formula (II-3) can be prepared by reacting a compound of the formula (II-1) with a compound of the formula (II-2) in the presence of an equivalent or more amount of a base in an appropriate solvent at a temperature in the range of from −70° C. to a boiling point of the solvent for from 0.5 to 24 hours.

The same base and solvent as illustrated in the above Preparation Process (1) can be used also in this step.

Step (b)

The compound of the formula (II-5) can be prepared by reacting a compound of the formula (II-3) (in the case that $R^4$ is a hydrogen atom) with a compound of the formula (II-4) in the presence of an equivalent or more amount of a base in an appropriate solvent at a temperature in the range of from −70° C. to a boiling point of the solvent for from 0.5 to 24 hours.

The same base and solvent as illustrated in the above Preparation Process (1) can be used also in this step.

Step (d)

The compound of the formula (II-4) can be prepared by stirring a compound of the formula (II-3) in the presence of an equivalent or more amount of a base in water or an appropriate solvent containing water at a temperature in the range of from room temperature to a boiling point of the solvent for from 0.5 to 24 hours and then acidifying.

As the base, there can be used alkali metal hydroxides such as sodium hydroxide and potassium hydroxide; alkali metal carbonates such as sodium carbonate and potassium carbonate; and alkali metal hydrogen carbonates such as sodium hydrogen carbonate and potassium hydrogen carbonate. As the solvent, there can be used hydrocarbon type solvents such as benzene, toluene and xylene; halogenated hydrocarbon type solvents such as methylene chloride and chloroform; alcohol type solvents such as methanol, ethanol and 2-propanol; ether type solvents such as diethyl ether, tetrahydrofuran and 1,4-dioxane; ketone type solvents such as acetone and methylethylketone; aprotic polar solvents such as dimethylformamide, dimethylacetamide and dimethylsulfoxide; and other acetonitrile and the like.

Step (e)

The compound of the formula (II-7) can be prepared by reacting a compound of the formula (II-6) with a compound of the formula (II-4) in the presence of an equivalent or more amount of a base in an appropriate solvent at a temperature in the range of from −70° C. to a boiling point of the solvent for from 0.5 to 24 hours.

The same base and solvent as illustrated in the above Preparation Process (1) can be used also in this step.

Step (c), Step (f) and Step (g)

The compound of the formula (II) can be prepared by stirring a compound of the formula (II-3), (II-5) or (II7) in the presence of an equivalent or more amount of a base in water or an appropriate solvent containing water at a temperature in the range of from room temperature to a boiling point of the solvent for from 0.5 to 24 hours.

The same base and solvent as illustrated in the above Step (d) can be used also in this step.

BEST MODE OF CARRYING OUT THE INVENTION

Now, concrete examples of the compound of the formula (I) are illustrated in the following Table 1. Compound numbers given in the Table will be referred to in the subsequent description.

TABLE 1

Structure:
$$\begin{array}{c} X-C(=N)-N(Z)-C(=N)-Y \\ \text{with central } C(R^3)(R^4)-CONR^1R^2 \end{array}$$

| Compound No. | $R^1$ | $R^2$ | $R^3$ | $R^4$ | X | Y | Z | Melting point (°C.) Refractive index ($n_D^{20}$) |
|---|---|---|---|---|---|---|---|---|
| 1 | H | $NH_2$ | phenyl | H | $OCH_3$ | $OCH_3$ | CH | 119–122 |
| 2 | H | $NHSO_2CH_3$ | phenyl | H | $OCH_3$ | $OCH_3$ | CH | Not measurable |
| 3 | H | $NH_2$ | 2-Cl-phenyl | H | $OCH_3$ | $OCH_3$ | CH | 108–111 |
| 4 | H | $NHSO_2CH_3$ | 2-Cl-phenyl | H | $OCH_3$ | $OCH_3$ | CH | Not measurable |
| 5 | H | $NH_2$ | 3-Cl-phenyl | H | $OCH_3$ | $OCH_3$ | CH | 97–99 |
| 6 | H | $NHSO_2CH_3$ | 3-Cl-phenyl | H | $OCH_3$ | $OCH_3$ | CH | 119–123 |
| 7 | $CH_2CH=CH_2$ | $SO_2CH_3$ | phenyl | H | $OCH_3$ | $OCH_3$ | CH | 1.5450 |

TABLE 1-continued

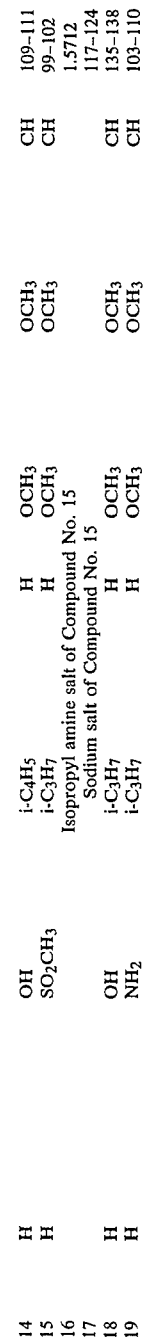

| Compound No. | R¹ | R² | R³ | R⁴ | X | Y | Z | Melting point (°C.) Refractive index ($n_D^{20}$) |
|---|---|---|---|---|---|---|---|---|
| 8 | CH₂COOC₂H₅ | (4-methylphenyl) | H | OCH₃ | OCH₃ | CH | | 1.5272 |
| 9 | H | SO₂CH₃ | (3-chlorophenyl) | H | OCH₃ | OCH₃ | CH | Not measurable |
| 10 | H | SO₂CH₃ | cyclopentyl | H | OCH₃ | OH | CH | 220-224 |
| 11 | H | SO₂CH₃ | phenyl | H | OCH₃ | OCH₃ | CH | 129-131 |
| 12 | CH₃ | SO₂CH₃ | phenyl | CH₃ | OCH₃ | OCH₃ | CH | 92-98 |
| 13 | H | SO₂CH₃ | phenyl | H | OCH₃ | OCH₃ | CH | 1.5475 |
| 14 | H | OH | i-C₄H₅ | H | OCH₃ | OCH₃ | CH | 109-111 |
| 15 | H | SO₂CH₃ | i-C₃H₇ | H | OCH₃ | OCH₃ | CH | 99-102 |
| 16 | Isopropyl amine salt of Compound No. 15 | | | | | | | 1.5712 |
| 17 | Sodium salt of Compound No. 15 | | | | | | | 117-124 |
| 18 | H | OH | i-C₃H₇ | H | OCH₃ | OCH₃ | CH | 135-138 |
| 19 | H | NH₂ | i-C₃H₇ | H | OCH₃ | OCH₃ | CH | 103-110 |

TABLE 1-continued

Structure:

$$\underset{X}{\overset{N}{\diagdown}}\underset{}{\overset{N}{\diagup}}\underset{Y}{\overset{N}{\diagdown}}\text{—}C(R^3)(R^4)\text{—}CON(R^1)(R^2)$$

| Compound No. | R¹ | R² | R³ | R⁴ | X | Y | Z | Melting point (°C.) Refractive index ($n_D^{20}$) |
|---|---|---|---|---|---|---|---|---|
| 20 | H | SO$_2$CH$_3$ | i-C$_4$H$_9$ | H | OCH$_3$ | OCH$_3$ | CH | 60-61 |
| 21 | H | SO$_2$CH$_3$ | i-C$_5$H$_{11}$ | H | OCH$_3$ | OCH$_3$ | CH | 81-82 |
| 22 | H | SO$_2$CH$_3$ | C$_3$H$_7$ | H | OCH$_3$ | OCH$_3$ | CH | 78-79 |
| 23 | H | SO$_2$CH$_3$ | CH$_2$CH=CH$_2$ | H | OCH$_3$ | OCH$_3$ | CH | 73-75 |
| 24 | H | SO$_2$CH$_3$ | [cyclopentyl] | H | OCH$_3$ | OCH$_3$ | CH | 97-99 |
| | | | Sodium salt of Compound No. 24 | | | | | |
| 25 | H | SO$_2$CH$_3$ | C$_4$H$_9$ | H | OCH$_3$ | OCH$_3$ | CH | 121-129 |
| 26 | H | SO$_2$CH$_3$ | i-C$_3$H$_7$ | CH$_3$ | OCH$_3$ | OCH$_3$ | CH | 69-70 |
| 27 | H | SO$_2$CH$_3$ | C$_5$H$_{11}$ | H | OCH$_3$ | OCH$_3$ | CH | 1.4917 |
| 28 | H | SO$_2$CH$_3$ | C$_3$H$_7$ | H | OCH$_3$ | OCH$_3$ | CH | 55-59 |
| 29 | H | OH | C$_3$H$_7$ | H | OCH$_3$ | OCH$_3$ | CH | 89-93 |
| 30 | H | SO$_2$CH$_3$ | [4-methylcyclohex-3-en-1-yl] | H | OCH$_3$ | OCH$_3$ | CH | 100-103 |
| 31 | H | NHSO$_2$CH$_3$ | i-C$_3$H$_7$ | H | OCH$_3$ | OCH$_3$ | CH | 125-131 |
| 32 | H | SO$_2$CH$_3$ | CH$_2$Si(CH$_3$)$_3$ | H | OCH$_3$ | OCH$_3$ | CH | 101-105 |
| 33 | H | NH$_2$ | [3-chlorophenyl] | H | OCH$_3$ | OCH$_3$ | CH | 129-132 |
| 34 | H | SO$_2$CH$_3$ | [2-methyltetrahydrothiophen-2-yl] | H | OCH$_3$ | OCH$_3$ | CH | 130-134 |
| 35 | H | NH$_2$ | [2-methylcyclopentyl] | H | OCH$_3$ | OCH$_3$ | CH | 127-134 |

TABLE 1-continued

[Structure: X-C(=N)-N=C(Y)-N(Z)- ring with -C(R³)(R⁴)-CON(R¹)(R²) substituent]

| Compound No. | R¹ | R² | R³ | R⁴ | X | Y | Z | Melting point (°C.) / Refractive index ($n_D^{20}$) |
|---|---|---|---|---|---|---|---|---|
| 36 | H | SO₂CH₃ | —CH₂—(cyclopropyl) | H | OCH₃ | OCH₃ | CH | 92–94 |
| 37 | H | SO₂CH₃ | cyclohexyl | H | OCH₃ | OCH₃ | CH | 91–93 |
| 38 | H | SO₂CH₃ | CH₃ | CH₃ | OCH₃ | OCH₃ | CH | 1.5028 |
| 39 | H | SO₂CH₃ | i-C₅H₁₁ | H | OCH₃ | Cl | CH | 159–165 |
| 40 | CH₃ | OCH₃ | s-C₄H₃ | H | OCH₃ | OCH₃ | CH | 1.4951 |
| 41 | H | SO₂CH₃ | CH(CH₃)(phenyl) | H | OCH₃ | OCH₃ | CH | Not measurable |
| 42 | H | SO₂CH₃ | CH₂–(cyclobutyl) | H | OCH₃ | OCH₃ | CH | 91–95 |
| 43 | H | SO₂CH₃ | CH₂–(cyclopentyl) | H | OCH₃ | OCH₃ | CH | 70–73 |
| 44 | H | SO₂CH₃ | CH₂–(cyclohexyl) | H | OCH₃ | OCH₃ | CH | 60–65 |
| 45 | H | SO₂CH₂Cl | i-C₃H₇ | H | OCH₃ | OCH₃ | CH | 116–118 |

TABLE 1-continued

[Structure: X-C(=N)-N=C(Y)-N=C(Z)- central ring with substituent -C(R³)(R⁴)-CON(R¹)(R²)]

| Compound No. | R¹ | R² | R³ | R⁴ | X | Y | Z | Melting point (°C.) Refractive index ($n_D^{20}$) |
|---|---|---|---|---|---|---|---|---|
| 46 | H | SO₂CH₃ | CH₂-C₆H₄-CH₃ (tolyl) | H | OCH₃ | OCH₃ | CH | |
| 47 | H | OCH₃ | i-C₄H₃ | H | OCH₃ | OCH₃ | CH | 1.4969 |
| 48 | H | SO₂CH₃ | CH(CH₃)(C₃H₇) | H | OCH₃ | OCH₃ | CH | 1.5023 |
| 49 | H | SO₂CH₃ | CH(CH₃)(C₃H₇) | H | OCH₃ | OC₂H₅ | CH | 1.5039 |
| 50 | H | SO₂CH₃ | s-C₄H₃ | H | OCH₃ | OCH₃ | CH | 97–101 |
| 51 | | | Sodium salt of Compound No. 50 | | | | | 88–103 |
| 52 | H | SO₂CH₃ | CH₂-C₆H₅ | H | OCH₃ | OCH₃ | CH | 104–106 |
| 53 | H | SO₂CH₃ | CH(C₂H₅)(C₂H₅) | H | OCH₃ | OCH₃ | CH | 99–102 |
| 54 | H | SO₂CH₃ | CH(C₂H₅)(C₃H₇) | H | OCH₃ | OCH₃ | CH | 1.5011 |
| 55 | H | SO₂CH₃ | i-C₃H₇ | H | CH₃ | CH₃ | CH | 118–119 |

TABLE 1-continued

Structure:
$$\begin{array}{c} X \\ | \\ N \\ \end{array} \underset{Z}{\overset{R^3}{\underset{|}{C}}} \underset{N}{\overset{R^4}{\underset{|}{C}}} \underset{Y}{\overset{CON}{\underset{R^2}{\overset{R^1}{}}}}$$

| Compound No. | R$^1$ | R$^2$ | R$^3$ | R$^4$ | X | Y | Z | Melting point (°C.) Refractive index ($n_D^{20}$) |
|---|---|---|---|---|---|---|---|---|
| 56 | H | SO$_2$CH$_3$ | cyclopentyl | H | CH$_3$ | CH$_3$ | CH | 150-153 |
| 57 | H | SO$_2$CH$_3$ | CH$_2$CH$_2$OH | H | OCH$_3$ | OCH$_3$ | CH | 106-110 |
| 58 | H | SO$_2$CH$_3$ | CH$_2$CH$_2$OC$_2$H$_5$ | H | OCH$_3$ | OCH$_3$ | CH | 1.5041 |
| 60 | H | SO$_2$CH$_3$ | CH$_3$ | H | OCH$_3$ | OCH$_3$ | CH | 121-122 |
| 61 | H | SO$_2$CH$_3$ | C$_2$H$_5$ | H | OCH$_3$ | OCH$_3$ | CH | 82-83 |
| 62 | H | SO$_2$CH$_3$ | CH$_2$CH=C(CH$_3$)CH$_3$ | H | OCH$_3$ | OCH$_3$ | CH | 81-85 |
| 63 | H | SO$_2$CH$_3$ | i-C$_3$H$_7$ | H | OCH$_3$ | CH$_3$ | CH | 116-117 |
| 64 | H | SO$_2$CH$_3$ | CH$_2$CCl=CH$_2$ | H | OCH$_3$ | OCH$_3$ | CH | 105-107 |
| 65 | H | SO$_2$CH$_3$ | C$_6$H$_{13}$ | H | OCH$_3$ | OCH$_3$ | CH | 72-74 |
| 66 | H | SO$_2$C$_2$H$_5$ | cyclopentyl | H | OCH$_3$ | OCH$_3$ | CH | 91-92 |
| 67 | H | SO$_2$C$_3$H$_7$ | cyclopentyl | H | OCH$_3$ | OCH$_3$ | CH | 75-77 |
| 68 | H | SO$_2$CH$_3$ | t-C$_4$H$_9$ | H | OCH$_3$ | OCH$_3$ | CH | 85-87 |
| 69 | H | SO$_2$C$_2$H$_5$ | s-C$_4$H$_9$ | H | OCH$_3$ | OCH$_3$ | CH | 97-101 |
| 70 | H | SO$_2$C$_3$H$_7$ | s-C$_4$H$_9$ | H | OCH$_3$ | OCH$_3$ | CH | 1.5069 |
| 71 | H | SO$_2$CF$_3$ | cyclopentyl | H | OCH$_3$ | OCH$_3$ | CH | 109-110 |

TABLE 1-continued $$\begin{array}{c}\text{structure with } X-C(=N)-N(Z)-C(=N)-Y, \text{ with } R^3, R^4, C, CON, R^1, R^2\end{array}$$

| Compound No. | R¹ | R² | R³ | R⁴ | X | Y | Z | Melting point (°C.) Refractive index ($n_D^{20}$) |
|---|---|---|---|---|---|---|---|---|
| 72 | H | SO₂CF₃ | i-C₄H₃ | H | OCH₃ | OCH₃ | CH | 1.4711 |
| 73 | H | SO₂CH₃ | CH₂C≡CH | H | OCH₃ | OCH₃ | CH | 107-109 |
| 74 | CH₃ | SO₂CH₃ | s-C₄H₃ | H | OCH₃ | OCH₃ | CH | 1.5092 |
| 75 | CH₂CH=CH₂ | SO₂CH₃ | i-C₃H₇ | H | OCH₃ | OCH₃ | CH | 1.5188 |
| 76 | H | SO₂CH₃ | CH₂CH₂-Ph | H | OCH₃ | OCH₃ | CH | 119-121 |
| 77 | H | SO₂CF₃ | i-C₃H₇ | H | OCH₃ | OCH₃ | CH | 121-123 |
| 78 | CH₂C≡CH | SO₂CH₃ | i-C₃H₇ | H | OCH₃ | OCH₃ | CH | 123-124 |
| 79 | CH₂OCH₃ | SO₂CH₃ | i-C₃H₇ | H | OCH₃ | OCH₃ | CH | 1.4976 |
| 80 | CH₂-Ph | SO₂CH₃ | i-C₃H₇ | H | OCH₃ | OCH₃ | CH | 123-124 |
| 81 | C₂H₅ | SO₂CH₃ | i-C₃H₇ | H | OCH₃ | OCH₃ | CH | 1.5075 |
| 82 | CH₂-Ph | SO₂CH₃ | s-C₄H₃ | H | OCH₃ | OCH₃ | CH | 118-119 |
| 83 | H | SO₂CH₃ | cyclopentyl | H | Cl | OCH₃ | CH | 149-151 |
| 84 | H | SO₂CH₃ | i-C₃H₇ | H | Cl | OCH₃ | CH | 144-146 |
| 85 | H | SO₂CH₃ | cyclopentyl | H | OCHF₂ | OCH₃ | CH | 124-126.5 |

TABLE 1-continued

Structure: 
$$\underset{X}{\overset{R^3}{\underset{N}{\bigvee}}}\underset{Z}{\overset{\overset{R^1}{\underset{R^4}{C-CON}}\overset{R^2}{}}{\bigvee}}\underset{Y}{\overset{N}{\bigvee}}$$

| Compound No. | R¹ | R² | R³ | R⁴ | X | Y | Z | Melting point (°C.) Refractive index ($n_D^{20}$) |
|---|---|---|---|---|---|---|---|---|
| 86 | H | SO₂CH₃ | cyclopentyl | H | N(CH₃)₂ | OCH₃ | CH | 112–115 |
| 87 | H | SO₂CH₃ | cyclopentyl | H | OCH₂C≡CH | OCH₃ | CH | 104–109 |
| 88 | H | SO₂CH₃ | cyclopentyl | H | o-CH₃-C₆H₄-O | OCH₃ | CH | 105–108 |
| 89 | H | o-Cl-C₆H₄ | s-C₄H₉ | H | OCH₃ | OCH₃ | CH | |
| 90 | H | o-CH₃-C₆H₄ | i-C₃H₇ | H | OCH₃ | OCH₃ | CH | 77–79 |
| 91 | H | C₆H₅ | cyclopentyl | H | OCH₃ | OCH₃ | CH | 123–125.5 |
| 92 | H | CN | cyclopentyl | H | OCH₃ | OCH₃ | CH | 90–95 |

TABLE 1-continued structure: X—C(=N)—N=C(Y)—Z with C(R³)(R⁴)—CON(R¹)(R²)

| Compound No. | R¹ | R² | R³ | R⁴ | X | Y | Z | Melting point (°C.) Refractive index ($n_D^{20}$) |
|---|---|---|---|---|---|---|---|---|
| 93 | H | SO₂CH₃ | CH₂CH₂O-phenyl | H | OCH₃ | OCH₃ | CH | 84-87 |
| 94 | H | SO₂CH₃ | CH₂SCH₃ | H | OCH₃ | OCH₃ | CH | |
| 95 | H | SO₂CH₃ | CH₂S-phenyl | H | OCH₃ | OCH₃ | CH | |
| 96 | H | SO₂CH₃ | CH₂CH₂N(CH₃)CH₃ | H | OCH₃ | OCH₃ | CH | |
| 97 | H | SO₂CH₃ | cyclopentyl | CH₃ | OCH₃ | OCH₃ | CH | 90-92 |
| 98 | H | SO₂CH₃ | cyclopentyl | C₂H₅ | OCH₃ | OCH₃ | CH | 1.5139 |
| 99 | H | SO₂CH₃ | cyclopentyl | C₃H₇ | OCH₃ | OCH | CH | |

TABLE 1-continued

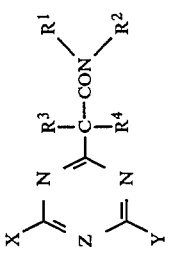

| Compound No. | R¹ | R² | R³ | R⁴ | X | Y | Z | Melting point (°C.) Refractive index ($n_D^{20}$) |
|---|---|---|---|---|---|---|---|---|
| 100 | H | SO$_2$CH$_3$ | cyclopentyl-CH$_3$ | H | OCH$_3$ | OCH$_3$ | CH | |
| 101 | H | SO$_2$CH$_3$ | cyclopentyl | H | OC$_2$H$_5$ | OCH$_3$ | CH | 104.5–106 |
| 102 | H | SO$_2$CH$_3$ | tetrahydrofuranyl | H | OCH$_3$ | OCH$_3$ | CH | |
| 103 | H | SO$_2$CH$_3$ | s-C$_4$H$_3$ | H | Cl | OCH$_3$ | CH | 144–148 |
| 104 | H | SO$_2$CH$_3$ | cyclopentyl | H | OC$_2$H$_5$ | OC$_2$H$_5$ | CH | 120.5–122.5 |
| 105 | H | SO$_2$CH$_3$ | cyclopentyl | H | OCH$_3$ | NHCH$_3$ | CH | 93–96 |
| 106 | H | SO$_2$CH$_3$ | cyclopentyl | H | OCH$_3$ | NHC$_2$H$_5$ | CH | 133.5–136.5 |

TABLE 1-continued
| Compound No. | R¹ | R² | R³ | R⁴ | X | Y | Z | Melting point (°C.) Refractive index ($n_D^{20}$) |
|---|---|---|---|---|---|---|---|---|
| 107 | H | SO$_2$CH$_3$ |  | H | OCH$_3$ | NHC$_3$H$_7$ | CH | 163–166 |
| 108 | H | SO$_2$CH$_3$ |  | H | OCH$_3$ | N(C$_2$H$_5$)(C$_2$H$_5$) | CH | 1.537-9 |
| 109 | H | SO$_2$CH$_3$ |  | H | OCH$_3$ |  | CH | 119–120.5 |
| 110 | H | SO$_2$CH$_3$ |  | H | OCH$_3$ | CF$_3$ | CH | |
| 111 | H | SO$_2$CH$_3$ |  | H | CH$_3$ | CF$_3$ | CH | |
| 112 | H | SO$_2$CH$_3$ |  | H | CH$_3$ | CH$_2$OCH$_3$ | CH | |
| 113 | H |  | s-C$_4$H$_3$ | H | OCH$_3$ | OCH$_3$ | CH | |

TABLE 1-continued
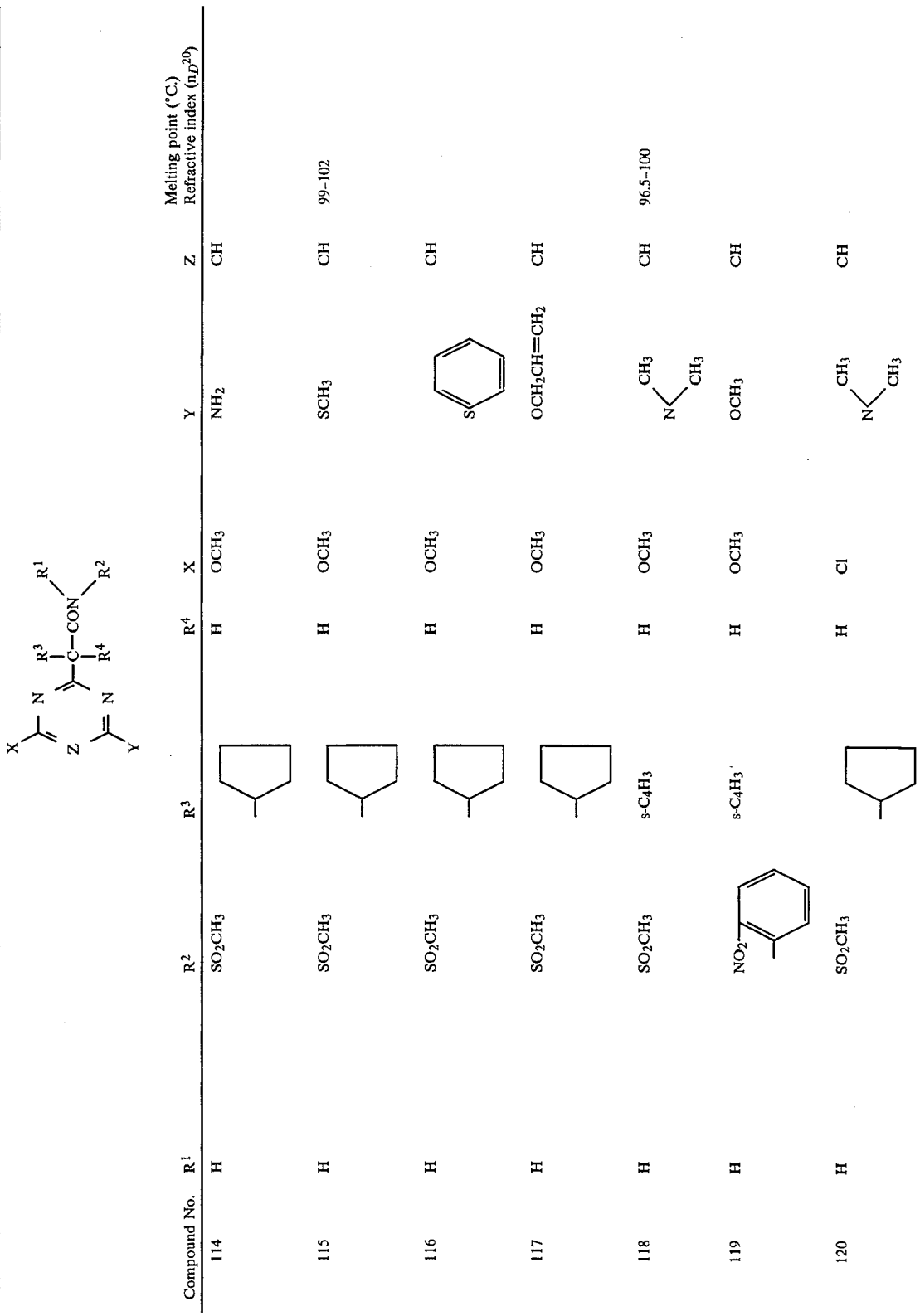
| Compound No. | $R^1$ | $R^2$ | $R^3$ | $R^4$ | X | Y | Z | Melting point (°C.) Refractive index ($n_D^{20}$) |
|---|---|---|---|---|---|---|---|---|
| 114 | H | $SO_2CH_3$ | cyclopentyl | H | $OCH_3$ | $NH_2$ | CH | |
| 115 | H | $SO_2CH_3$ | cyclopentyl | H | $OCH_3$ | $SCH_3$ | CH | 99–102 |
| 116 | H | $SO_2CH_3$ | cyclopentyl | H | $OCH_3$ | $S$-phenyl | CH | |
| 117 | H | $SO_2CH_3$ | cyclopentyl | H | $OCH_3$ | $OCH_2CH=CH_2$ | CH | |
| 118 | H | $SO_2CH_3$ | s-$C_4H_3$ | H | $OCH_3$ | $N(CH_3)_2$ | CH | 96.5–100 |
| 119 | H | 2-$NO_2$-phenyl | s-$C_4H_3$ | H | $OCH_3$ | $OCH_3$ | CH | |
| 120 | H | $SO_2CH_3$ | cyclopentyl | H | Cl | $N(CH_3)_2$ | CH | |

TABLE 1-continued

| Compound No. | R¹ | R² | R³ | R⁴ | X | Y | Z | Melting point (°C.) Refractive index ($n_D^{20}$) |
|---|---|---|---|---|---|---|---|---|
| 121 | H | SO$_2$CH$_3$ | cyclopentyl | H | OCH$_3$ | OCH$_3$ | N | |
| 122 | H | SO$_2$CH$_3$ | s-C$_4$H$_3$ | H | OCH$_3$ | OCH$_3$ | N | |
| 123 | H | SO$_2$CH$_3$ | cyclopentyl | H | OCH$_3$ | N(CH$_3$)CH$_3$ | N | |
| 124 | H | SO$_2$CH$_3$ | s-C$_4$H$_3$ | H | OCH$_3$ | N(CH$_3$)CH$_3$ | N | |
| 125 | H | SO$_2$CH$_3$ | cyclopentyl | H | OCH$_3$ | NHCH$_3$ | N | |
| 126 | H | SO$_2$CH$_3$ | s-C$_4$H$_3$ | H | OCH$_3$ | NHCH$_3$ | N | |
| 127 | H | SO$_2$CH$_3$ | cyclopentyl | H | OCH$_3$ | CH$_3$ | N | |
| 128 | H | SO$_2$CH$_3$ | s-C$_4$H$_3$ | H | OCH$_3$ | CH$_3$ | N | |
| 129 | H | SO$_2$CH$_3$ | t-C$_4$H$_3$ | H | OCH$_3$ | CH$_3$ | N | |
| 130 | CH$_2$OCH$_3$ | SO$_2$CH$_3$ | s-C$_4$H$_3$ | H | OCH$_3$ | OCH$_3$ | CH | 1.4998 |
| 131 | CH$_2$OC$_2$H$_5$ | SO$_2$CH$_3$ | s-C$_4$H$_3$ | H | OCH$_3$ | OCH$_3$ | CH | 1.4971 |

TABLE 1-continued

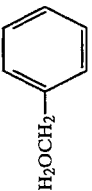

| Compound No. | $R^1$ | $R^2$ | $R^3$ | $R^4$ | X | Y | Z | Melting point (°C.) Refractive index ($n_D^{20}$) |
|---|---|---|---|---|---|---|---|---|
| 132 | CH$_2$OCH$_2$⟨phenyl⟩ | SO$_2$CH$_3$ | s-C$_4$H$_3$ | H | OCH$_3$ | OCH$_3$ | CH | 1.5321 |
| 133 | CH$_2$SCH$_3$ | SO$_2$CH$_3$ | s-C$_4$H$_3$ | H | OCH$_3$ | OCH$_3$ | CH | 1.5269 |
| 134 | CH$_2$OCH$_2$CH$_2$OCH$_3$ | SO$_2$CH$_3$ | s-C$_4$H$_3$ | H | OCH$_3$ | OCH$_3$ | CH | 1.4999 |
| 135 | CH$_2$COOCH$_3$ | SO$_2$CH$_3$ | s-C$_4$H$_3$ | H | OCH$_3$ | OCH$_3$ | CH | 1.4986 |
| 136 | CH$_2$OCH$_3$ | SO$_2$CH$_3$ | ⟨cyclopentyl⟩ | H | OCH$_3$ | OCH$_3$ | CH | 1.5139 |
| 137 | CH$_2$OC$_2$H$_3$ | SO$_2$CH$_3$ | ⟨cyclopentyl⟩ | H | OCH$_3$ | OCH$_3$ | CH | 1.5090 |
| 138 | CH$_2$SCH$_3$ | SO$_2$CH$_3$ | ⟨cyclopentyl⟩ | H | OCH$_3$ | OCH$_3$ | CH | 1.5374 |
| 139 | CH$_2$OCH$_2$CH$_2$OCH$_3$ | SO$_2$CH$_3$ | ⟨cyclopentyl⟩ | H | OCH$_3$ | OCH$_3$ | CH | 1.5103 |
| 140 | CH$_2$COOCH$_3$ | SO$_2$CH$_3$ | ⟨cyclopentyl⟩ | H | OCH$_3$ | OCH$_3$ | CH | 1.5121 |

TABLE 1-continued

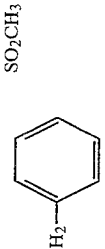

| Compound No. | R¹ | R² | R³ | R⁴ | X | Y | Z | Melting point (°C.) Refractive index ($n_D^{20}$) |
|---|---|---|---|---|---|---|---|---|
| 141 | CH₂OCH₂—C₆H₅ | SO₂CH₃ | cyclopentyl-CH₃ | H | OCH₃ | OCH₃ | CH | 1.5412 |
| 142 | OH | SO₂CH₃ | s-C₄H₃ | H | OCH₃ | OCH₃ | CH | 129–131 |
| 143 | OCH₂—C₆H₅ | SO₂CH₃ | s-C₄H₃ | H | OCH₃ | OCH₃ | CH | 1.5282 |
| 144 | OCH₂CH=CH₂ | SO₂CH₃ | s-C₄H₃ | H | OCH₃ | OCH₃ | CH | 1.5065 |
| 145 | OCH₂C≡CH | SO₂CH₃ | s-C₄H₃ | H | OCH₃ | OCH₃ | CH | |
| 146 | OCH₃ | SO₂CH₃ | cyclopentyl-CH₃ | H | OCH₃ | OCH₃ | CH | 1.5426 |
| 147 | H | SO₂CH₂OCH | s-C₄H₃ | H | OCH₃ | OCH₃ | CH | 1.5065 |
| 148 | H | SO₂CH₂OC₂H₅ | s-C₄H₃ | H | OCH₃ | OCH₃ | CH | 1.5016 |
| 149 | H | SO₂CH₂OC₃H₇-i | s-C₄H₃ | H | OCH₃ | OCH₃ | CH | 1.4992 |
| 150 | H | SO₂C₃H₇-i | s-C₄H₃ | H | OCH₃ | OCH₃ | CH | 1.5033 |
| 151 | H | cyclopentyl-SO₂ | s-C₄H₃ | H | OCH₃ | OCH₃ | CH | 99–101 |
| 152 | H | SO₂CH₂CH=CH₂ | s-C₄H₃ | H | OCH₃ | OCH₃ | CH | |
| 153 | H | SO₂C₄H₃-s | s-C₄H₃ | H | OCH₃ | OCH₃ | CH | |
| 154 | H | SO₂CH₂OCH | cyclopentyl-CH₃ | H | OCH₃ | OCH₃ | CH | 1.5126 |

TABLE 1-continued $$\begin{array}{c} R^1 \\ | \\ R^3 \quad C-CON \\ \diagdown / \quad \diagup \quad R^4 \quad R^2 \\ N \quad N \\ \| \quad \| \\ X \quad Z \quad Y \end{array}$$

| Compound No. | R¹ | R² | R³ | R⁴ | X | Y | Z | Melting point (°C.) Refractive index ($n_D^{20}$) |
|---|---|---|---|---|---|---|---|---|
| 155 | H | SO₂CH₂OC₂H₅ | cyclopentyl | H | OCH₃ | OCH₃ | CH | 1.5149 |
| 156 | H | SO₂CH₂OC₃H₇ | cyclopentyl | H | OCH₃ | OCH₃ | CH | 1.5074 |
| 157 | H | SO₂C₃H₇-i | cyclopentyl | H | OCH₃ | OCH₃ | CH | 90.5–92 |
| 158 | H | SO₂-cyclopentyl | cyclopentyl | H | OCH₃ | OCH₃ | CH | 93–95 |
| 159 | H | SO₂CH₂CH=CH₂ | cyclopentyl | H | OCH₃ | OCH₃ | CH | |
| 160 | H | SO₂C₄H₃-s | cyclopentyl | H | OCH₃ | OCH₃ | CH | |
| 161 | H | SO₂CH₃ | cyclopentyl | H | OCH₃ | OCH₃ | CH | 108–110 |
| 162 | H | OH | s-C₄H₃ | H | OCH₃ | OCH₃ | CH | 136–140 |

TABLE 1-continued

Structure:
$$\begin{array}{c} X \\ \diagdown \\ N \\ \| \\ \end{array} \begin{array}{c} R^1 \\ \diagdown \\ R^3-C-CON \\ | \quad \diagdown \\ R^4 \quad R^2 \\ \end{array}$$
with ring containing N, Z, N and Y substituent.

| Compound No. | R¹ | R² | R³ | R⁴ | X | Y | Z | Melting point (°C.) Refractive index ($n_D^{20}$) |
|---|---|---|---|---|---|---|---|---|
| 163 | H | —OCH₂—(phenyl) | s-C₄H₃ | H | OCH₃ | OCH₃ | CH | 1.5355 |
| 164 | H | OCH₂CH=CH₂ | s-C₄H₃ | H | OCH₃ | OCH₃ | CH | 1.5085 |
| 165 | H | OH | (cyclopentyl) | H | OCH₃ | OCH₃ | CH | 1.5205 |
| 166 | H | SO₂N(pyrrolidine) | (cyclopentyl) | H | OCH₃ | OCH₃ | CH | |
| 167 | H | SO₂N(CH₃)₂ | (cyclopentyl) | H | OCH₃ | OCH₃ | CH | |
| 168 | H | SO₂NHCH₃ | (cyclopentyl) | H | OCH₃ | OCH₃ | CH | |
| 169 | H | SO₂NH—(phenyl) | (cyclopentyl) | H | OCH₃ | OCH₃ | CH | |

Now, a process for preparing the compound of the present invention is more concretely explained hereinafter by Reference Example and Examples.

REFERENCE EXAMPLE

Preparation of 2-(4,6-dimethoxypyrimidin-2-yl)-3-methylbutyric acid (1) 6.0 g of diethyl 2-isopropylmalonate, 1.2 g of 60% sodium hydride and 50 ml of N,N-dimethylformamide were placed in a round bottom flask, and are stirred at 60° C. for 30 minutes. Thereafter, 4.7 g of 4,6-dimethoxy-2-fluoropyrimidine was added thereto. After stirring for further 5 hours, 100 ml of water was added to the resultant reaction liquor, and the reaction liquor was extracted twice with 100 ml of ether. This extracted liquor was washed with water, and was dried with anhydrous sodium sulfate for one night. After filtrating the inorganic salt, the solvent was distilled off under reduced pressure to obtain 7.2 g of a viscous liquid. The viscous liquor thus obtained was purified by silica gel column chromatography (developing solvent: n-hexane/ethyl acetate=5/1) to obtain 6.6 g of diethyl 2-(4,6-dimethoxypyrimidin-2-yl)-2-isopropylmalonate (yield=64.7%). Light yellow liquid, refractive index (n20/D)=1.4808.

(2) 10 g of diethyl 2-(4,6-dimethoxypyrimidin-2-yl)-2-isopropylmalonate, 5,0 g of sodium hydroxide, 20 ml of water and 50 ml of methanol were placed in a round bottom flask, and were stirred under heat-refluxing for 6 hours. The reaction liquor was concentrated, and 100 ml of water was added thereto. The reaction liquor was adjusted to a pH of from 3 to 4 with a dilute hydrochloric acid under cooling with ice, and was extracted twice with 100 ml of diethyl ether. The extracted liquor was washed with water, and was dried with anhydrous sodium sulfate for one night. After filtrating the inorganic salt, the solvent was distilled off under reduced pressure to obtain 5.8 g of a crude crystal. The crude crystal thus obtained was recrystallized from ether-hexane to obtain 5.3 g of the aimed product of white powder (yield=75.1%) having a melting point of 99°–101° C.

EXAMPLE 1

Preparation of 2-(4,6-dimethoxypyrimidin-2-yl)-3-methyl-1-N-methylsulfonylbutyric acid amide (Compound No. 15)

(1) 5.0 g of 2-(4,6-dimethoxypyrimidin-2-yl)-3methylbutyric acid prepared in accordance with the above Reference Example method, 3.4 g of carbonyldiimidazole and 50 ml of tetrahydrofuran were placed in a round bottom flask, and were stirred at room temperature for 1 hour. Thereafter, this reaction mixture was poured in ice water, and was extracted twice with 50 ml of diethyl ether. This extracted liquor was washed with water, and was dried with anhydrous sodium sulfate for one night. After filtrating the inorganic salt, the solvent was distilled off under reduced pressure. A crude crystal thus obtained was washed with hexane to obtain 5.2 g of 2-(4,6-dimethoxypyrimidin-2-yl)-3-methylbutyrylimidazole of colorless needle-like crystal (yield=86.7%) having a melting point of 74°–78° C.

(2) 1.7 of methanesulfoneamide, 0.7 g of 60% sodium hydride and 50 ml of N,N-dimethylformamide were placed in a round bottom flask, and were stirred at room temperature for 1 hour. Thereafter, to the resultant reaction liquor, was added 5.0 g of 2-(4,6-dimethoxypyrimidin-2-yl)-3-methylbutyrylimidazole at room temperature, and the resultant reaction liquor was stirred at room temperature for 1 hour. This reaction mixture was poured into ice water, and the reaction mixture was adjusted to a pH of about 3 with a dilute hydrochloric acid and was extracted twice with 100 ml of ethyl acetate. This extracted liquor was washed with water, and was dried with anhydrous sodium sulfate for one night. After filtrating the inorganic salt, the solvent was distilled off under reduced pressure to obtain 4.5 g of a crude crystal. The crude crystal thus obtained was recrystallized from diethyl ether to obtain 4.2 g of the aimed product of colorless needle-like crystal (yield=76.8%) having a melting point of 99°–102° C.

EXAMPLE 2

Preparation of 2-(4,6-dimethoxypyrimidin-2-yl)-N-methoxymethyl-3-methyl-N-methylsulfonylbutyric acid amide (Compound No. 79)

2.0 of 2-(4,6-dimethoxypyrimidin-2-yl)-3-methyl-N-methylsulfonylbutyric acid amide was placed in a round bottom flask, and was dissolved in 50 ml of DMF. To the resultant solution, was gradually added 0.28 g of 60% sodium hydride, and the mixture was stirred at room temperature for one hour. Thereafter, 1.0 g of chloromethyl ethyl ether was added dropwise to the resultant mixture, and the mixture was stirred at room temperature for 2 hours. The reaction mixture was then poured into ice water, and was extracted with 200 ml of diethyl ether, followed by drying with anhydrous sodium sulfate. After filtrating the inorganic salt, the solvent was distilled off under reduced pressure. An only product thus obtained was purified by silica gel column chromatography (developing solvent: N-hexane/ethyl acetate=10/1) to obtain 1.8 g of the aimed product of colorless transparent viscous liquid (yield=78.3%) having a refractive index (n20/D) of 1.4976.

EXAMPLE 3

Preparation of sodium salt of 2-(4,6-dimethoxypyrimidin-2-yl)-3-methyl-N-methylsulfonylbutyric acid amide (Compound No. 17)

1.5 g of 2-(4.6-dimethoxypyrimidin-2-yl)-3-methyl-N-methylsulfonylbutyric acid amide was dissolved in 20 ml of methanol, and 0.9 g of 28% sodium methoxide was added to the resultant solution to obtain a uniform solution. The solvent was distilled off under reduced pressure, and a crude crystal thus obtained was washed with diethyl ether to obtain 1.5 g of the aimed product of white powder (yield=93.8%) having a melting point of 117°–124° C. (decomposition).

EXAMPLE 4

Preparation of 3-cyclopropyl-2-(4,6-dimethoxypyrimidin-2-yl)-N-methylsulfonylpropionic acid amide (Compound No. 36)

3.0 g of 3-cyclopropyl-2-(4,6-dimethoxypyrimidin-2yl)propionic acid, 1.2 g of methanesulfone amide and 20 ml of pyridine were placed in a round bottom flask, and 1.5 g of thionylchloride was added dropwise thereto while stirring under cooling with ice. After stirring at room temperature for 3 hours, the reaction mixture was poured into ice water, and the reaction mixture was adjusted a pH of about 3 with a dilute hydrochloric acid and was extracted twice with 100 ml of ethyl acetate. This extracted liquor was washed with water and was dried with anhydrous sodium sulfate for one night. After filtrating the inorganic salt, the solvent was distilled off under reduced pressure to obtain 3.5 g of viscous liquid. The viscous liquid thus obtained was purified by silica gel column chromatography (developing solvent=hexane/ethyl acetate=3/1) to obtain 2.8 g of the aimed product of colorless needle-like crystal (yield=71.5%) having a melting point of 92°-94° C.

EXAMPLE 5

Preparation of 2-(4,6-dimethoxypyrimidin-2-yl)-3-methyl-N-methyl-sulfonylvaleric acid amide (compound No. 50)

5.0 g of 2-(4,6-dimethoxypyrimidin-2-yl)-3methylvaleric acid butyric acid, 3.2 g of carbonyldiimidazole and 30 ml of N,N-dimethylformamide were placed in a round bottom flask, and were stirred at room temperature for 1 hour. 1.9 g of methanesulfone amide, 0.8 g of 60% sodium hydride and 20 ml of N,N-dimethylformamide were placed in a round bottom flask, and were stirred at room temperature for 1 hour. To the resultant mixture, was dropwise added at room temperature the N,N-dimethylformamide solution of 2-(4,6-dimethoxypyrimidin-2-yl)-3-methylpentanoylimidazole prepared as mentioned above, and the resultant mixture was stirred at room temperature for 3 hours. This reaction mixture was then poured into ice water, and the mixture was adjusted to a pH of about 3 with a dilute hydrochloric acid and was extracted twice with 100 ml of ethyl acetate. This extracted liquor was washed with water, and was dried with anhydrous sodium sulfate for one night. After filtrating the inorganic salt, the solvent was distilled off to obtain 5.8 g of a crude crystal. The crude crystal thus obtained was recrystallized from diethyl ether to obtain 5.4 g of the aimed compound of colorless needle-like crystal (yield=82.9%) having a melting point of 97-101° C.

EXAMPLE 6

Preparation of 2-cyclopentyl-2-(4,6-dimethoxypyrimidin-2-yl)-3-methoxycarbonylmethyl -N-methylsulfonylacetoamide (Compound No. 140)

1.5 g of 2-cyclopentyl-2-(4,6-dimethoxypyrimidin-2-yl)-N-methylsulfonylacetoamide, 0.8 g of potassium carbonate and 30 ml of DMF were placed in a round bottom flask. To the resultant mixture, was dropwise added 0.8 g of methyl bromoacetate, and the mixture was stirred at room temperature for 8 hours. The reaction liquor was then poured into water, and was extracted with 200 ml of ethyl acetate and the extracted liquor was dried with anhydrous sodium sulfate. After filtrating the inorganic salt, the solvent was distilled off under reduced pressure. An only product thus obtained was purified by silica gel chromatography (developing solvent: hexane/methyl acetate=10/1) to obtain 1.5 g of the aimed product of colorless transparent viscous liquid (yield=83.3%) having a refractive index (n20/D) of 1.5121.

EXAMPLE 7

Preparation of isopropylamine salt of 2-(4,6-dimethoxypyrimidin-2-yl)-3-methyl-N-methyl-sulfonylbutyric acid amide (Compound No. 16)

1.9 g of 2-(4,6-dimethoxypyrimidin-2-yl)-3-methyl-N-methylsulfonylbutyric acid amide, 0.4 g of isopropylamine and 20 ml of tetrahydrofuran were placed in a round bottom flask, and were made into a completely uniform solution. Thereafter, the solvent was distilled off under reduced pressure to obtain 2.2 g of the aimed product of light yellow glassy material (yield=97.6%) having a refractive index (n20/D) of 1.5712.

The herbicidal composition of the present invention comprises the pyrimidine derivative of the general formula [I]and its salt as an effective ingredient. When the compound of the present invention is applied as a herbicide to paddy fields, upland fields, fruit garden, nonagriculture lands or the like, the effective ingredient may be applied in various formulations depending on its use object. Generally, the herbicide of the present invention may be used as it is or may be formulated in various formulations which are commonly used as herbicidal compositions, such as a powder, a wettable powder, a granule, an emulsifiable concentrate or by blending it with an inert liquid or solid carrier, a surfactant, a dispersing agent or an adjuvant which is commonly employed for the formulation of agricultural chemicals. As the carrier to be used for the formulation, there may be mentioned a solid carrier such as Jeeklight, talc, bentonite, clay, kaolin, diatomaceous earth, white carbon, vermiculite, slaked lime, silica sand, ammonium sulfate or urea, or a liquid carrier such as isopropyl alcohol, xylene, cyclohexanone or methyl naphthalene. As the surfactant and dispersing agent, there may be mentioned, for example, an alcohol-sulfuric acid ester, an alkylaryl sulfonate, lignin sulfonate, a polyoxyethylene glycol ether, a polyoxyethylene alkyl aryl ether or a polyoxyethylene sorbitol mono-alkylate as the adjuvant, for example, carboxymethyl cellulose, polyethylene glycol or gum arabic may be mentioned. The herbicide may be diluted to a suitable concentration before application, or may directly be applied.

The herbicide of the present invention is used by applying to foliage, soil or water surface. The proportion of the compound of the present invention in the formulation may optionally be selected, and it is optically selected from the range of from 0.01 to 20% by weight, preferably from the range of from 0.1 to 5% by weight for power or granule formulation, and it is optionally selected from the range of from 1 to 80% by weight, preferably from the range of from 5 to 20% by weight, for emulsifiable concentrate and wettable powder formulations. The dose of the herbicide of the present invention varies depending on the type of the compound used, the object weed, the grow tendency, the environmental condition and the formulation used, but it is optionally selected from the range of from 0.1 g to 5 kg/10 ares (as an active ingredient), preferably from the range of from 1 g to 1 kg/10 ares, for powder and granule formulations which are used as they are, and it is optionally selected from the range of from 0.1 to 10,000 ppm, preferably from the range of from 10 to 3,000 ppm, for emulsifiable concentrate and wettable powder formulations which are used in liquid.

If desired, the compound of the present invention may be used in combination with insecticides, sterilizers, other herbicides, plant growth controlling agents, fertilizers or the like.

Now, typical Formulation Examples for the herbicidal composition of the present invention will be given. In these Examples, "part" means "part by weight".

FORMULATION EXAMPLE 1 (wettable powder)

10 parts of Compound No. 6, 0.5 part of polyoxyethylene alkylaryl ether, 0.5 part of sodium naphthalenesulfonate-formalin condensate, 20 parts of diatomaceous earth and 69 parts of clay were uniformly mixed and pulverized to obtain a wettable powder.

FORMULATION EXAMPLE 2 (wettable powder)

10 parts of Compound No. 11, 0.5 part of polyoxyethylene alkylaryl ether, 0.5 part of sodium naphthalenesulfonate-formalin condensate, 20 parts of diatomaceous earth 201, 5 parts of Carplex 80 and 64 parts of clay were uniformly mixed and pulverized to obtain a wettable powder.

FORMULATION EXAMPLE 3 (emulsifiable concentrate)

30 Parts of Compound No. 14, 60 parts of equivalent amount mixture of xylene and isophorone, and 10 parts of a mixture of polyoxyethylene alkylaryl ether and a metal salt of alkylbenzene sulfonic acid were uniformly mixed and stirred to obtain an emulsifiable concentrate.

FORMULATION EXAMPLE 4 (granule)

10 Parts of Compound No. 26, 80 parts of a bulking agent comprising a 1:3 mixture of talc and bentonite, 5 parts of white carbon, 5 parts of a mixture of polyoxyethylene alkylaryl ether and a metal salt of alkylbenzene sulfonic acid and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

FORMULATION EXAMPLE 5 (powder)

1 part of Compound No. 26 and 99 parts of diatomaceous each were mixed and pulverized to obtain powder.

The compound of the formula (I) and its salt of the present invention achieve excellent herbicidal effects at a very small dose on annual weeds such as barnyardgrass (Echinochloa crus-qualli), small flower flatsedge (Cyperus diffomis) and monochoria (Monochoria vaqinalis), and perennial weeds such as Sagittaria pygmaea, Cyperus serotinus, Elecharis kuroguwa$_i$, bulrush (Scirpus hotarui) and Alisma canaliculatum, grown in paddy fields in a wide range of from germination to growth periods. Furthermore, the herbicide of the present invention is capable of effectively killing various weeds grown in upland fields, such as wide-leaf weeds including smartweed (Polygonum lapthifolium), slender amaranth (Amaranthus viridis), lambsquarters (Chenopodium album), chickweed (Stellaria media), velvetleaf (Abutilon theophrasti), prickly sida (Side spinosa), morningglory (Ipomoes spp) and common cocklebur (Xanthium strumarium); perennial and annual umbrellaplant (Cyperus microiria) family weeds including purple nusedge (Cyperus rotundus), yellow nutsedge, Kyllinga brevifolia, Cyperus microiria and Cyperus iria; and gramineous weeds including barnyardglass (Echinochloa crus-qalli), carbgrass (Digitaria ciliaris), green foxtail (Setaria viridis), annual bluegrass (Poa annua), johnsongrass (Sorghum halepense), water foxtail (Alopecurus aequalis) and wild oat (Avena fatua).

On the other hand, the herbicides of the present invention are highly safe to crop plants, particularly rice, wheat, barley, soybean, cotton or the like.

Now, the herbicidal activities of the compounds of the present invention will be described with reference to Test Examples.

TEST EXAMPLE 1 (Herbicidal effect test by paddy field soil treatment)

In a pot filled with paddy field soil (surface area: 100 cm$^2$), seeds of barnyardgrass (Ec), monochoria (Mo) and bulrush (Sc) were sown, and water was introduced to a depth of 3 cm. One day later from the seeding, a predetermined amount of wettable powder prepared in accordance with Formulation Example 1, was diluted with water and dropwise applied to the water surface in a dose of 100 g of the active ingredient per 10 ares. After growing in a green house, the herbicidal effect was evaluated on the 21st day after the treatment in accordance with the standard as identified in Table 2. The results are shown by the index numbers in Table 3. The following compounds as disclosed in U.S. Pat. No. 4,427,437 were tested as Comparative Examples.

Comparative Compound No. 1

Ethyl 3-(5-chloropyrimidin-2-yloxy)benzoate

Comparative Compound No. 2

Ethyl 5-(5-chloropyrimidin-2-yloxy)-2-nitrobenzoate

TABLE 2

| Index | Herbicidal effect and phytotoxicity (Growth-controlling degree) |
|---|---|
| 5 | Herbicidal effect, phytotoxicity: at least 90% |
| 4 | Herbicidal effect, phytotoxicity: at least 70% and less than 90% |
| 3 | Herbicidal effect, phytotoxicity: at least 50% and less than 70% |
| 2 | Herbicidal effect, phytotoxicity: at least 30% and less than 50% |
| 1 | Herbicidal effect, phytotoxicity: at least 10% and less than 30% |
| 0 | Herbicidal effect, phytotoxicity: at least 0% and less than 10% |

TABLE 3

| Compound No. | Herbicidal effect | | |
|---|---|---|---|
| | Ec | Mo | Sc |
| 6 | 5 | 5 | 5 |
| 9 | 5 | 5 | 4 |
| 11 | 5 | 5 | 5 |
| 13 | 5 | 5 | 5 |
| 14 | 5 | 5 | 5 |
| 15 | 5 | 5 | 4 |
| 16 | 5 | 5 | 5 |
| 17 | 5 | 5 | 5 |
| 18 | 4 | 5 | 4 |
| 19 | 5 | 5 | 5 |
| 20 | 5 | 5 | 5 |
| 21 | 5 | 5 | 5 |
| 22 | 5 | 5 | 5 |
| 24 | 5 | 5 | 5 |
| 25 | 5 | 5 | 5 |
| 26 | 5 | 5 | 5 |
| 30 | 5 | 5 | 5 |
| 31 | 5 | 4 | 4 |
| 33 | 5 | 5 | 5 |
| 36 | 5 | 5 | 5 |
| 37 | 5 | 5 | 3 |
| 44 | 5 | 5 | 3 |
| 48 | 5 | 5 | 5 |
| 49 | 5 | 5 | 5 |
| 50 | 5 | 5 | 5 |
| 51 | 5 | 5 | 5 |
| 53 | 5 | 5 | 5 |
| 54 | 5 | 5 | 5 |

TABLE 3-continued

| Compound No. | Herbicidal effect | | |
|---|---|---|---|
| | Ec | Mo | Sc |
| 63 | 5 | 5 | 4 |
| 64 | 5 | 5 | 5 |
| 66 | 5 | 5 | 5 |
| 67 | 5 | 5 | 5 |
| 68 | 5 | 5 | 5 |
| 69 | 5 | 5 | 5 |
| 70 | 5 | 5 | 5 |
| 74 | 5 | 4 | 5 |
| 79 | 5 | 5 | 5 |
| 80 | 4 | 5 | 5 |
| 82 | 5 | 5 | 4 |
| 83 | 5 | 5 | 5 |
| 84 | 5 | 5 | 5 |
| 86 | 5 | 5 | 5 |
| 87 | 5 | 5 | 5 |
| 88 | 5 | 5 | 3 |
| 92 | 5 | 5 | 4 |
| 97 | 5 | 5 | 4 |
| 101 | 5 | 5 | 5 |
| 103 | 5 | 5 | 5 |
| 104 | 5 | 5 | 4 |
| 105 | 5 | 5 | 5 |
| 106 | 5 | 5 | 3 |
| 118 | 5 | 5 | 5 |
| 130 | 5 | 5 | 5 |
| 131 | 5 | 5 | 5 |
| 132 | 5 | 5 | 5 |
| 133 | 5 | 5 | 5 |
| 134 | 5 | 5 | 4 |
| 136 | 5 | 5 | 5 |
| 137 | 5 | 5 | 5 |
| 138 | 5 | 5 | 5 |
| 139 | 5 | 5 | 3 |
| 141 | 5 | 5 | 5 |
| 142 | 5 | 5 | 5 |
| 144 | 5 | 5 | 4 |
| 146 | 5 | 5 | 5 |
| 150 | 5 | 4 | 5 |
| 151 | 5 | 5 | 3 |
| 154 | 5 | 5 | 3 |
| 157 | 5 | 5 | 5 |
| 158 | 5 | 5 | 5 |
| 161 | 5 | 5 | 5 |
| 162 | 5 | 5 | 5 |
| 166 | 5 | 5 | 3 |
| Comparative Compound No. 1 | 0 | 0 | 0 |
| Comparative Compound No. 2 | 0 | 0 | 0 |

TEST EXAMPLE 2 (Herbicidal effect test by upland field soil treatment)

In a plastic pot filled with upland field soil (surface area: 120 cm$^2$), barnyardgrass (Ec), pale smartweed (Po), slender amaranth (Am), lambsquarters (Ch) and Cyperus iria (Ci) were sown and covered with soil. Next day, a predetermined amount of a wettable powder prepared in accordance with Formulation Example 1 was diluted with water and applied uniformly to the soil surface by a small-sized sprayer in an amount of 100 1/10 ares so that the dose of the active ingredient was 100 g/10 ares. The pot was then cultured in a green house, and the herbicidal effect was evaluated on the 21st day after the treatment in accordance with the standard as identified in Table 2. The test results are shown in the following Table 4.

TABLE 4

| Compound No. | Herbicidal effect | | | | |
|---|---|---|---|---|---|
| | Ec | Po | Am | Ch | Ci |
| 7 | 4 | 4 | 5 | 5 | 5 |
| 9 | 4 | 5 | 5 | 5 | 5 |

TABLE 4-continued

| Compound No. | Herbicidal effect | | | | |
|---|---|---|---|---|---|
| | Ec | Po | Am | Ch | Ci |
| 11 | 4 | 5 | 5 | 5 | 5 |
| 13 | 5 | 4 | 4 | 4 | 5 |
| 14 | 4 | 5 | 5 | 5 | 5 |
| 16 | 5 | 5 | 5 | 5 | 5 |
| 17 | 5 | 5 | 5 | 5 | 5 |
| 18 | 5 | 5 | 5 | 5 | 5 |
| 20 | 5 | 5 | 5 | 5 | 5 |
| 21 | 5 | 3 | 5 | 5 | 5 |
| 22 | 5 | 5 | 5 | 5 | 5 |
| 24 | 5 | 5 | 5 | 5 | 5 |
| 25 | 5 | 5 | 5 | 5 | 5 |
| 26 | 5 | 5 | 5 | 5 | 5 |
| 28 | 5 | 5 | 5 | 5 | 5 |
| 36 | 5 | 5 | 5 | 5 | 5 |
| 37 | 5 | 5 | 5 | 5 | 5 |
| 42 | 2 | 5 | 5 | 5 | 4 |
| 43 | 5 | 5 | 5 | 5 | 5 |
| 44 | 5 | 5 | 5 | 5 | 5 |
| 48 | 5 | 5 | 5 | 5 | 5 |
| 49 | 5 | 5 | 5 | 5 | 5 |
| 50 | 5 | 5 | 5 | 5 | 5 |
| 51 | 5 | 5 | 5 | 5 | 5 |
| 53 | 5 | 5 | 5 | 5 | 5 |
| 54 | 5 | 5 | 5 | 5 | 5 |
| 56 | 5 | 5 | 5 | 4 | 5 |
| 63 | 5 | 5 | 5 | 5 | 5 |
| 64 | 5 | 5 | 5 | 5 | 5 |
| 65 | 3 | 5 | 5 | 4 | 5 |
| 66 | 5 | 5 | 5 | 5 | 5 |
| 67 | 5 | 5 | 5 | 5 | 5 |
| 68 | 5 | 5 | 5 | 5 | 5 |
| 69 | 5 | 5 | 5 | 5 | 5 |
| 70 | 5 | 5 | 5 | 5 | 5 |
| 83 | 5 | 5 | 5 | 5 | 5 |
| 84 | 5 | 5 | 5 | 5 | 5 |
| 85 | 5 | 5 | 5 | 5 | 5 |
| 86 | 5 | 5 | 5 | 5 | 5 |
| 87 | 4 | 5 | 5 | 5 | 5 |
| 92 | 4 | 5 | 5 | 5 | 5 |
| 97 | 3 | 5 | 5 | 5 | 5 |
| 101 | 5 | 5 | 5 | 5 | 5 |
| 103 | 5 | 5 | 5 | 5 | 5 |
| 104 | 5 | 5 | 5 | 5 | 5 |
| 105 | 5 | 5 | 5 | 5 | 5 |
| 106 | 4 | 5 | 5 | 5 | 5 |
| 107 | 4 | 4 | 5 | 5 | 5 |
| 108 | 5 | 4 | 5 | 5 | 5 |
| 118 | 5 | 5 | 5 | 5 | 5 |
| 130 | 4 | 4 | 5 | 5 | 5 |
| 131 | 4 | 4 | 5 | 5 | 5 |
| 132 | 3 | 5 | 5 | 5 | 5 |
| 133 | 3 | 5 | 5 | 5 | 5 |
| 136 | 5 | 5 | 5 | 5 | 5 |
| 137 | 5 | 5 | 5 | 5 | 5 |
| 138 | 4 | 5 | 5 | 5 | 5 |
| 141 | 4 | 5 | 5 | 5 | 5 |
| 142 | 5 | 5 | 5 | 4 | 5 |
| 144 | 5 | 5 | 5 | 5 | 5 |
| 146 | 2 | 5 | 5 | 5 | 5 |
| 150 | 5 | 5 | 5 | 5 | 5 |
| 157 | 4 | 5 | 5 | 5 | 5 |
| 162 | 4 | 5 | 5 | 5 | 5 |

TEST EXAMPLE 3 (Herbicidal effect test by upland field foliage treatment)

In a plastic pot filled with upland field soil (surface area: 120 cm$^2$), barnyardgrass (Ec), pale smartweed (Po), slender amaranth (Am), lambsquarters (Ch) and Cyperus iria (Ci) were sown and grown in a green house for two weeks. thereafter, a predetermined amount of a wettable powder prepared in accordance with Formulation Example 1 was diluted with water and applied onto the foliage from above by a small-sized sprayer in an amount of 100 1/10 ares so that the dose of the active ingredient was 100 g/10 ares. The pot was then cultured in a green house, and the herbicidal effect was evaluated on the 14th day after the treatment in accordance with the standard as identified in Table 2. The test results are shown in the following Table 5.

TABLE 5

| Compound No. | Herbicidal effect | | | | |
| --- | --- | --- | --- | --- | --- |
| | Ec | Po | Am | Ch | Ci |
| 8 | 3 | 4 | 5 | 5 | 5 |
| 9 | 4 | 5 | 5 | 5 | 5 |
| 11 | 5 | 5 | 5 | 5 | 5 |
| 15 | 5 | 5 | 5 | 5 | 5 |
| 16 | 5 | 5 | 5 | 5 | 5 |
| 17 | 5 | 5 | 5 | 5 | 5 |
| 20 | 5 | 5 | 5 | 5 | 5 |
| 21 | 4 | 5 | 4 | 5 | 5 |
| 22 | 5 | 5 | 5 | 4 | 5 |
| 24 | 5 | 5 | 5 | 5 | 5 |
| 25 | 5 | 5 | 5 | 5 | 5 |
| 26 | 4 | 5 | 5 | 5 | 5 |
| 30 | 2 | 5 | 5 | 5 | 4 |
| 36 | 5 | 5 | 5 | 5 | 5 |
| 37 | 4 | 5 | 3 | 5 | 2 |
| 44 | 5 | 5 | 5 | 5 | 5 |
| 45 | 3 | 5 | 5 | 3 | 5 |
| 48 | 5 | 5 | 5 | 5 | 5 |
| 49 | 5 | 5 | 5 | 4 | 5 |
| 50 | 5 | 5 | 5 | 5 | 5 |
| 51 | 5 | 5 | 5 | 5 | 5 |
| 53 | 5 | 5 | 5 | 5 | 5 |
| 54 | 5 | 5 | 5 | 5 | 3 |
| 56 | 5 | 4 | 5 | 4 | 5 |
| 63 | 5 | 5 | 5 | 5 | 5 |
| 64 | 5 | 5 | 5 | 5 | 5 |
| 66 | 5 | 5 | 5 | 5 | 5 |
| 67 | 5 | 5 | 5 | 5 | 5 |
| 68 | 5 | 5 | 5 | 5 | 5 |
| 69 | 5 | 5 | 5 | 5 | 5 |
| 70 | 5 | 5 | 5 | 5 | 5 |
| 79 | 5 | 5 | 5 | 5 | 5 |
| 83 | 5 | 5 | 5 | 5 | 5 |
| 84 | 5 | 5 | 5 | 5 | 5 |
| 85 | 5 | 5 | 5 | 5 | 5 |
| 86 | 5 | 5 | 5 | 5 | 5 |
| 87 | 5 | 5 | 5 | 5 | 5 |
| 97 | 4 | 4 | 5 | 5 | 5 |
| 101 | 5 | 5 | 5 | 5 | 5 |
| 103 | 4 | 5 | 5 | 5 | 5 |
| 104 | 5 | 5 | 5 | 5 | 5 |
| 105 | 5 | 5 | 5 | 5 | 5 |
| 106 | 4 | 5 | 5 | 5 | 4 |
| 108 | 5 | 5 | 5 | 5 | 5 |
| 118 | 5 | 5 | 5 | 5 | 5 |
| 130 | 5 | 5 | 5 | 5 | 3 |
| 131 | 5 | 5 | 5 | 5 | 3 |
| 132 | 4 | 5 | 5 | 5 | 5 |
| 133 | 4 | 5 | 5 | 5 | 5 |
| 134 | 4 | 4 | 5 | 5 | 5 |
| 136 | 4 | 5 | 5 | 5 | 5 |
| 137 | 5 | 5 | 5 | 5 | 5 |
| 138 | 5 | 5 | 5 | 5 | 5 |
| 141 | 5 | 5 | 5 | 5 | 5 |
| 143 | 4 | 4 | 5 | 5 | 5 |
| 144 | 4 | 5 | 5 | 5 | 5 |
| 146 | 3 | 5 | 4 | 5 | 5 |
| 150 | 5 | 5 | 5 | 5 | 5 |
| 157 | 5 | 5 | 5 | 5 | 5 |
| 162 | 3 | 5 | 5 | 5 | 5 |

TEST EXAMPLE 4 (Herbicidal effect and phytotoxicity tests by upland field soil treatment)

In a plastic pot filled with upland field soil (surface area: 600 cm²), soybean (Gl), cotton (Go), barnyardgrass (Ec), pale smartweed (Po), slender amaranth (Am), lambsquarters (Ch), velvetleaf (Ab) and morningglory (Ip) were sown, and a tuber of purple nutsedge (Cr) was placed and covered with soil. After absorbing water from the bottom of the pot, a predetermined amount (ai, g/10a) of a wettable powder prepared in accordance with Formulation Example 1 was diluted with water in an amount of 100 l/10 ares and applied uniformly to the soil surface by a small-sized sprayer. The pot was then cultured in a green house, and the herbicidal effect and the phytotoxicity were evaluated on the 20th day after the treatment in accordance with the standard as identified in Table 2. The test results are shown in the following Table 6.

TABLE 6

| Compound No. | Dose g/10a | Phytotoxicity | | Herbicidal effect | | | | | | |
| --- | --- | --- | --- | --- | --- | --- | --- | --- | --- | --- |
| | | Gl | Go | Ec | Po | Am | Ch | Ab | Ip | Cr |
| 15 | 25 | 2 | 1 | 5 | 5 | 5 | 5 | 5 | 4 | 4 |
| 16 | 25 | 0 | 0 | 4 | 5 | 5 | 5 | 4 | 4 | 4 |
| 17 | 25 | 2 | 1 | 5 | 5 | 5 | 5 | 4 | 4 | 5 |
| 20 | 25 | 2 | 0 | 5 | 5 | 5 | 5 | 5 | 5 | 5 |
| 24 | 25 | 2 | 1 | 5 | 5 | 5 | 5 | 4 | 3 | 5 |
| 25 | 25 | 2 | 1 | 5 | 5 | 5 | 5 | 5 | 4 | 5 |
| 26 | 25 | 0 | 1 | 4 | 4 | 5 | 5 | 5 | 3 | 5 |
| 36 | 25 | 2 | 0 | 5 | 5 | 5 | 5 | 5 | 4 | 5 |
| 48 | 25 | 1 | 0 | 5 | 5 | 5 | 5 | 5 | 5 | 5 |
| 50 | 25 | 0 | 0 | 5 | 5 | 5 | 5 | 5 | 5 | 5 |
| 53 | 25 | 0 | 0 | 5 | 5 | 5 | 5 | 5 | 3 | 3 |
| 67 | 25 | 0 | 2 | 2 | 5 | 5 | 5 | 4 | 3 | 2 |
| 68 | 25 | 1 | 1 | 5 | 5 | 5 | 5 | 5 | 5 | 5 |
| 69 | 25 | 2 | 1 | 5 | 5 | 5 | 5 | 5 | 5 | 5 |
| 86 | 25 | 2 | 0 | 5 | 5 | 5 | 5 | 5 | 4 | 5 |
| 101 | 25 | 3 | 1 | 5 | 5 | 5 | 5 | 5 | 5 | 5 |
| 105 | 25 | 1 | 0 | 5 | 5 | 5 | 5 | 5 | 5 | 5 |
| 118 | 25 | 0 | 0 | 5 | 5 | 5 | 5 | 5 | 5 | 5 |
| 130 | 25 | 3 | 0 | 5 | 5 | 5 | 5 | 5 | 5 | 5 |
| 131 | 25 | 2 | 0 | 5 | 5 | 5 | 5 | 5 | 5 | 5 |
| 137 | 25 | 3 | 0 | 5 | 5 | 5 | 5 | 5 | 5 | 5 |
| 150 | 25 | 1 | 1 | 5 | 5 | 5 | 4 | 5 | 5 | 5 |

We claim:

1. An alkanoic acid amide derivative having the following formula (I) and its salt:

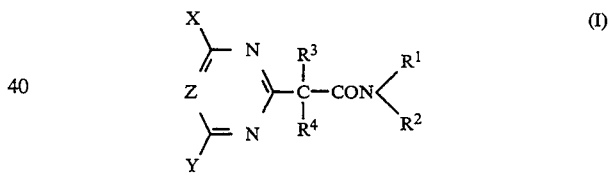

wherein $R^1$ is a hydroxy group, a $C_2$-$C_8$ alkyl group, a $C_1$-$C_8$ alkyl group (which may be substituted with a $C_1$-$C_8$ alkoxy group, a benzyloxy group, a $C_1$-$C_8$ alkoxy-$C_1$-$C_8$ alkoxy group, a $C_1$-$C_8$ alkoxycarbonyl group, a $C_1$-$C_3$ alkylthio group or a phenyl group), a $C_2$-$C_6$ alkenyl group, a $C_2$-$C_6$ alkynyl group, a $C_1$-$C_8$ alkoxy group, a benzyloxy group, a $C_2$-$C_6$ alkenyloxy group or a $C_2$-$C_6$ alkynyloxy group; $R^2$ is a hydroxy group, a $C_1$-$C_8$ alkoxy group, a benzyloxy group, a $C_2$-$C_6$ alkenyloxy group, a cyano group, a phenyl group (which may be substituted with a $C_1$-$C_8$ alkyl group, a trifluoromethyl group, a halogen atom or a nitro group), an amino group, a $C_1$-$C_8$ alkylsulfonylamino group or a group of -$SO_2R^5$ ($R^5$ is a $C_1$-$C_8$ alkyl group (which may be substituted with a $C_1$-$C_8$ alkoxy group or a halogen atom), a $C_2$-$C_6$ alkenyl group, a $C_3$-$C_8$ cycloalkyl group, a $C_1$-$C_8$ alkylamino group, a di-$C_1$-$C_8$-alkylamino group, a 1-pyrrolydinyl group or an anilino group); $R^3$ is a $C_1$-$C_8$ alkyl group (which may be substituted with a hydroxy group, a $C_1$-$C_8$ alkoxy group, a phenoxy group, a $C_1$-$C_8$ alkylthio group, a phenylthio group, a trimethylsilyl group, a $C_3$-$C_8$ cycloalkyl group, a phenyl group or a di-$C_1$-$C_8$-alkylamino group), a $C_2$-$C_6$ alkenyl group (which may be substituted with a halogen atom), a $C_2$-$C_6$ alkynyl group, a $C_3$-$C_8$ cycloalkyl group (which may be substituted with a $C_1$-$C_8$ alkyl group), a $C_3$-$C_6$ cycloalkenyl group, a phenyl group (which may be substituted with a $C_1$-$C_8$ alkyl group or a halogen atom), a tetrahydrothienyl group or a tetrahydrofuryl group; $R^4$ is a hydrogen atom or a $C_1$-$C_8$ alkyl group; X and Y may be the same or different, and are a hydroxyl group, a halogen atom, a $C_1$-$C_8$ alkyl group, a $C_1$-$C_8$ haloalkyl group, a $C_1$-$C_8$ alkoxy-$C_1$-$C_8$-alkyl group, a $C_1$-$C_8$ alkoxy group, a phenoxy group (which may be substituted with a $C_1$-$C_8$ alkyl group), a $C_1$-$C_8$ haloalkoxy group, a $C_2$-$C_6$ alkenyloxy group, a $C_2$-$C_6$ alkynyloxy group, a $C_1$-$C_8$ alkylthio group, a phenylthio group, an amino group, a $C_1$-$C_8$ alkylamino group, a di-$C_1$-$C_8$-alkylamino group or a pyrrolidino group; and Z is a methine group.

2. The alkanoic acid amide derivative and its salt as claimed in claim 1, wherein $R^1$ is a $C_2$-$C_8$ alkyl group.

3. The alkanoic acid amide derivative and its salt as claimed in claim 1, wherein $R^1$ is a $C_1$-$C_8$ alkyl group substituted with a $C_1$-$C_8$ alkoxy group, a benzyloxy group, a $C_1$-$C_8$ alkoxy-$C_1$-$C_8$-alkoxy group, a $C_1$-$C_8$ alkoxycarbonyl group, a $C_1$-$C_3$ alkylthio group or a phenyl group.

4. A herbicidal composition comprising an effective amount of the alkanoic acid amide derivative or its salt as defined in claim 1 and a suitable carrier.

5. A method for killing weeds which comprises applying to a plant or soil, an effective amount of the alkanoic acid amide derivative or its salt as defined in claim 1.

6. An alkanoic acid amide derivative having the following formula (I) and its salt:

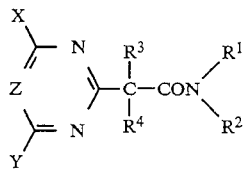

wherein $R^1$ is a hydroxy group, a $C_1$-$C_8$ alkyl group substituted with a $C_1$-$C_8$ alkoxy group, a benzyloxy group, a $C_1$-$C_8$ alkoxy-$C_1$-$C_8$-alkoxy group, a $C_1$-$C_8$ alkoxycarbonyl group, a $C_1$-$C_3$ alkylthio group or a phenyl group, a $C_2$-$C_6$ alkenyl group, a $C_2$-$C_6$ alkynyl group, a $C_1$-$C_8$ alkoxy group, a benzyloxy group, a $C_2$-$C_6$ alkenyloxy group or a $C_2$-$C_6$ alkynyloxy group; $R^2$ is a hydroxy group, a $C_1$-$C_8$ alkoxy group, a benzyloxy group, a $C_2$-$C_6$ alkenyloxy group, a cyano group, a phenyl group (which may be substituted with a $C_1$-$C_8$ alkyl group, a trifluoromethyl group, a halogen atom or a nitro group), an amino group, a $C_1$-$C_8$ alkylsulfonylamino group or a group of -$SO_2R^5$ ($R^5$ is a $C_1$-$C_8$ alkyl group (which may be substituted with a $C_1$-$C_8$ alkoxy group or a halogen atom), a $C_2$-$C_6$ alkenyl group, a $C_3$-$C_8$ cycloalkyl group, a $C_1$-$C_8$ alkylamino group, a di-$C_1$-$C_8$-alkylamino group, a 1-pyrrolydinyl group or an anilino group); $R^3$ is a hydrogen atom, a $C_1$-$C_8$ alkyl group (which may be substituted with a hydroxy group, a $C_1$-$C_8$ alkoxy group, a phenoxy group, a $C_1$-$C_8$ alkylthio group, a phenylthio group, a trimethylsilyl group, a $C_3$-$C_8$ cycloalkyl group, a phenyl group or a di-$C_1$-$C_8$-alkylamino group), a $C_2$-$C_6$ alkenyl group (which may be substituted with a halogen atom), a $C_2$-$C_6$ alkynyl group, a $C_3$-$C_8$ cycloalkyl group (which may be substituted with a $C_1$-$C_8$ alkyl group), a $C_3$-$C_6$ cycloalkenyl group, a phenyl group (which may be substituted with a $C_1$-$C_8$ alkyl group or a halogen atom), a tetrahydrothienyl group or a tetrahydrofuryl group; $R^4$ is a hydrogen atom or a $C_1$-$C_8$ alkyl group; X and Y may be the same or different, and are a hydroxyl group, a halogen atom, a $C_1$-$C_8$ alkyl group, a $C_1$-$C_8$ haloalkyl group, a $C_1$-$C_8$ alkoxy-$C_1$-$C_8$-alkyl group, a $C_1$-$C_8$ alkoxy group, a phenoxy group (which may be substituted with a $C_1$-$C_8$ alkyl group), a $C_1$-$C_8$ haloalkoxy group, a $C_2$-$C_6$ alkenyloxy group, a $C_2$-$C_6$ alkynyloxy group, a $C_1$-$C_8$ alkylthio group, a phenylthio group, an amino group, a $C_1$-$C_8$ alkylamino group, a di-$C_1$-$C_8$-alkylamino group or a pyrrolidino group; and Z is a methine group.

7. The alkanoic acid amide derivative and its salt claimed in claim 6 wherein $R^1$ is a $C_2$-$C_8$ alkyl group.

8. An alkanoic acid amide derivative having the following formula (I) and its salt:

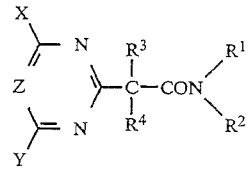

wherein $R^1$ is a hydroxy group, a $C_1$-$C_8$ alkyl group substituted with a $C_1$-$C_8$ alkoxy group, a benzyloxy group, a $C_1$-$C_8$ alkoxy-$C_1$-$C_8$-alkoxy group, a $C_1$-$C_8$ alkoxycarbonyl group, a $C_1$-$C_3$ alkylthio group or a phenyl group, a $C_2$-$C_6$ alkenyl group, a $C_2$-$C_6$ alkynyl group, a $C_1$-$C_8$ alkoxy group, a benzyloxy group, a $C_2$-$C_6$ alkenyloxy group or a $C_2$-$C_6$ alkynyloxy group; $R^2$ is a hydroxy group, a $C_1$-$C_8$ alkoxy group, a benzyloxy group, a $C_2$-$C_6$ alkenyloxy group, a cyano group, a phenyl group substituted with a $C_1$-$C_8$ alkyl group substituent, a trifluoromethyl group substituent, a halogen atom substituent, or a nitro group substituent, an amino group, a $C_1$-$C_8$ alkylsulfonylamino group or a group of -$SO_2R^5$ ($R^5$ is a $C_1$-$C_8$ alkyl group (which may be substituted with a $C_1$-$C_8$ alkoxy group or a halogen atom), a $C_2$-$C_6$ alkenyl group, a $C_3$-$C_8$ cycloalkyl group, a $C_1$-$C_8$ alkylamino group, a di-$C_1$-$C_8$-alkylamino group, a 1-pyrrolydinyl group or an anilino group); $R^3$ is a hydrogen atom, a $C_1$-$C_8$ alkyl group (which may be substituted with a hydroxy group, a $C_1$-$C_8$ alkoxy group, a phenoxy group, a $C_1$-$C_8$ alkylthio group, a phenylthio group, a trimethylsilyl group, a $C_3$-$C_8$ cycloalkyl group, a phenyl group or a di-$C_1$-$C_8$-alkylamino group), a $C_2$-$C_6$ alkenyl group (which may be substituted with a halogen atom), a $C_2$-$C_6$ alkynyl group, a $C_3$-$C_8$ cycloalkyl group (which may be substituted with a $C_1$-$C_8$ alkyl group), a $C_3$-$C_6$ cycloalkenyl group, a phenyl group (which may be substituted with a $C_1$-$C_8$ alkyl group or a halogen atom), a tetrahydrothienyl group or a tetrahydrofuryl group; $R^4$ is a hydrogen atom or a $C_1$-$C_8$ alkyl group; X and Y may be the same or different, and are a hydroxyl group, a halogen atom, a $C_1$-$C_8$ alkyl group, a $C_1$-$C_8$ haloalkyl group, a $C_1$-$C_8$ alkoxy-$C_1$-$C_8$-alkyl group, a $C_1$-$C_8$ alkoxy group, a phenoxy group (which may be substituted with a $C_1$-$C_8$ alkyl group), a $C_1$-$C_8$ haloalkoxy group, a $C_2$-$C_6$ alkenyloxy group, a $C_2$-$C_6$ alkynyloxy group, a $C_1$-$C_8$ alkylthio group, a phenylthio group, an amino group, a $C_1$-$C_8$ alkylamino group, a di-$C_1$-$C_8$-alkylamino group or a pyrrolidino group; and Z is a methine group.

9. A herbicidal composition comprising an effective amount of the alkanoic acid amide derivative or its salt as defined in claim 7 and a suitable carrier.

10. A method for killing weeds which comprises applying to a plant or soil, an effective amount of the alkanoic acid amide derivative or its salt as defined in claim 6.

11. A herbicidal composition comprising an effective amount of the alkanoic acid amide derivative or its salt as defined in claim 8 and a suitable carrier.

12. A method for killing weeds which comprises applying to a plant or soil, an effective amount of the alkanoic acid amide derivative or its salt as defined in claim 8.

* * * * *